US008318438B2

(12) United States Patent
Vivekananda et al.

(10) Patent No.: US 8,318,438 B2
(45) Date of Patent: Nov. 27, 2012

(54) APTAMER-BASED ASSAYS

(75) Inventors: Jeevalatha Vivekananda, San Antonio, TX (US); Johnathan L. Kiel, Universal City, TX (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 1254 days.

(21) Appl. No.: 12/072,758

(22) Filed: Feb. 27, 2008

(65) Prior Publication Data

US 2012/0157670 A1 Jun. 21, 2012

Related U.S. Application Data

(60) Provisional application No. 60/904,900, filed on Mar. 1, 2007.

(51) Int. Cl.
*C12Q 1/00* (2006.01)
*C12Q 1/68* (2006.01)
*G01N 33/00* (2006.01)
*G01N 33/554* (2006.01)
*G01N 33/569* (2006.01)

(52) U.S. Cl. .............. 435/6.15; 424/130.1; 424/139.1; 424/143.1; 424/150.1; 424/156.1; 424/164.1; 424/184.1; 424/185.1; 424/190.1; 424/193.1; 424/234.1; 424/278.1; 435/4; 435/6.1; 435/6.19; 435/7.32; 435/7.8; 435/7.92; 435/7.95; 435/29; 435/34; 435/39; 435/174; 435/243; 435/287.2

(58) Field of Classification Search ................ None
See application file for complete search history.

(56) References Cited

U.S. PATENT DOCUMENTS 6,569,630 B1   5/2003   Vivekananda et al.

OTHER PUBLICATIONS

Kiel et al., (2004 Scientific Conference on Chemical & Biological defense Research Nov. 15-18, 2004, Hunt Valley, Maryland).*
Thirumalapura (Application of Molecular Methods in Diagnostics of Bacterial Pathogens. Submitted to the Faculty of the Graduate College of the Oklahoma State University in partial fulfillment of the requirements for the Degree of Doctor of Philosophy. May 2005).*
Baldrich, et al. "Displacement Enzyme Linked Aptamer Assay," Anal. Chem. 2005, 77, 4774-4784.
Drolet DW, Moon-McDermott L, Romig TS. An enzyme-linked oligonucleotide assay. Nat Biotechnol 1996;8:1021-1025. (Only the abstract is attached.).

(Continued)

*Primary Examiner* — Ja'na Hines
(74) *Attorney, Agent, or Firm* — Paul Heydon; Rebecca Greendyke; AFMCLO/JAZ (57) ABSTRACT

We describe examples using aptamers for capturing and reporting the presence of a target, such as a pathogen. Examples described here include a set of aptamers that are specific to *F. tularensisis*. Other examples described here include an Aptamer-Linked Immobilized Sorbent Assay (AL-ISA) and dot blot assay. An example of a method provided here comprises: providing a set of DNA sequences that ex 
OTHER PUBLICATIONS Grunow R, Splettstoesser W, McDonald S, et al. Detection of *Francisella tularensis* in biological specimens using capture enzyme-linked immunosorbant assay, an immuno-chromatographic handheld assay and PCR. Clin Diag Lab Immunol 2000;7:86-90.

Lee M, Walt DR. A fiber-optic microarray biosensor using aptamers as receptors. Anal Biochem 2000;282: 142-146.

Liss M, Petersen B, Wolf H, et al. An aptamer-based quartz-crystal protein biosensor. Anal Chem 2002;74: 4488-4495.

Porsch-Ozcurumez M, Kischiel N, Priebe H, et al. Comparison of enzyme-linked immunosorbent assay, western blotting, muicroglutination, indirect immunofluorescence assay and flow cytometry for serological diagnosis of tularemia. Clin Diag Invest Immunol 2004;11:1008-1015.

Rye PD, Nustad K. Immunomagnetic DNA aptamer assay. Biotechniques 2001;30:290-295. (Only the abstract is attached.).

Vivekananda and Kiel, "Anti-*Francisella tularensis* DNA Aptamers Detect Tularemia Antigen From Different Subspecies by Aptamer-Linked Immobilized Sorbent Assay," Laboratory Investigation (2006) 86, 610-618 (published online Mar. 20, 2006).
Yang X, Li X, Prow TW, et al. Immunofluorescence assay and flow-cytometry selection of bead-bound aptamers. Nucleic Acids Res 2003;31:e54.

* cited by examiner

APTAMER-BASED ASSAYS

RELATED APPLICATION, AND RIGHTS OF THE GOVERNMENT

This application claims the benefit under 35 U.S.C. §119 (e) of provisional Patent Application Ser. No. 60/904,900, filed Mar. 1, 2007, the entire text of which is incorporated herein by reference.

The invention described herein may be manufactured and used by or for the Government of the United States for all governmental purposes without the payment of any royalty.

BACKGROUND OF THE INVENTION

The invention relates to assays and more particularly to capturing and reporting the presence of a target, such as a pathogen.

Interest in Francisella tularensis has increased recently because of its potential use as an agent of biological warfare. Francisella tularensis is an intracellular, nonmotile, nonsporulating, Gram-negative bacterial pathogen that causes tularemia in man and animals. Its extreme hardiness, infectivity and the ability to cause lethal disease by aerosol raise serious concern that this organism can be exploited by terrorists as a possible biological weapon. As a result, tularemia bacteria is one of the high ranking pathogens categorized by CDC as a category A agent with the greatest impact on public health if it is used as a weapon of mass destruction. Human tularemia manifests itself in a variety of syndromes, most of them depending on the portal of infection. The clinical appearance varies from skin lesions to multiorgan involvement. Furthermore, the severity depends on the dose and the virulence of the pathogen. Francisella tularensis subsp. holarctica (type B) which is spread over the northern hemisphere is less virulent than Francisella tularensis sub tularensis (type A) which is distributed mainly in North America and is associated with a severe and generally fatal form of tularemia. In particular, typhoid and pneumonic forms are the most deadly with mortality that can exceed 30% if patients are left untreated. The current diagnostic test for tularemia is a colorimetric immunoagglutination assay based on a type B tularemia target. This type is immunologically indistinguishable from type A, the more pathogenic type. The military is more concerned with type A because of its potential as a very potent biological warfare or bioterrorism agent. Currently, PCR can distinguish type A from type B, but only by a difference in size of a specific PCR product. Also, the "gold standard" for distinguishing the two is culture. Type A can ferment glycerol, but type B cannot. Because of the high infectivity of small quantities of the bacteria, culture is not usually done, except in BSL3 laboratories.

Thus, there is a need for sensitive diagnostic systems and highly durable, reliable field tests, especially concerning pathogens that are potential agents of biological warfare (for example, an assay to replace the current immunoagglutination and antibody-based ELISA assays for the diagnosis of tularemia).

SUMMARY OF THE INVENTION

We describe examples using aptamers for capturing and reporting the presence of a target, such as a pathogen. Examples described here include a set of aptamers that are specific to F. tularensisis. Other examples described here include an Aptamer-Linked Immobilized Sorbent Assay (ALISA) and dot blot assay. An example of a method provided here comprises: providing a set of DNA sequences that exhibit high binding affinity to target antigen, placing the DNA sequences in a sandwich aptamer-linked immobilized sorbent assay (ALISA), contacting the DNA sequences with a sample, and detecting whether the target is present in the sample. Some alternative implementations may include dot blots and different reporters. Quantum dot sandwich assays and quantum dot de-quenching reporters can be used.

DETAILED DESCRIPTION

We describe examples using aptamers for capturing and reporting the presence of a target, such as a pathogen. Aptamers are single-stranded oligonucleotides with a length of tens of nucleotides, exhibiting high affinity and specificity towards any given target molecule. Aptamers have highly defined tertiary structures, which allow them to form stable and specific complexes with a range of different targets including small molecules such as amino acids to highly complex proteins and whole viruses. For details of the examples, see the article by Jeevalatha Vivekananda and Johnathan L Kiel, "Anti-Francisella tularensis DNA Aptamers Detect Tularemia Antigen From Different Subspecies by Aptamer-Linked Immobilized Sorbent Assay," Laboratory Investigation (2006) 86, 610-618 (published online 20 Mar. 2006) hereby incorporated by reference.

Materials and Methods for Examples Described Below:

F. tularensis subspecies japonica killed bacterial antigen and its antiserum, trypticase soy broth (TSP), Brain heart infusion (Difco), the glycerol production and agglutination test kits were purchased from Becton Dickinson and Company, Sparks, Md., USA. F. tularensis subspecies holarctica live vaccine strain (type B) was obtained from the Centers for Disease Control and Prevention (CDC) (live vaccine strain Lot #11, NDBR 101 Lot 0200). F. tularensis subspecies tularensis (SCHU 4-type A) was received from Peter Emanuel of the Critical Reagent Collection of the Department of Defense Joint Program in Chemical and Biological Defense. F. tularensis type B (#38) was isolated from a cat in Houston, Tex., USA. Bartonella henselae (ATCC Number 49882) was purchased from American Type Culture Collection, Manassas, Va., USA. Bovine serum albumin fraction V, chicken albumin, lysozyme from chicken egg and other chemicals were obtained from Sigma. A synthetic random DNA library, biotin labeled primers and other primers were from Sigma/Genosys, The Woodlands, Tex., USA. Dot blot reagents and nitrocellulose membranes and biospin disposable chromatography columns were from Bio-Rad, Hercules, Calif., USA. Reagents for PCR were purchased from PGC Scientific (Gaithersburg, Md., USA) and Applied Biosystems (Foster City, Calif., USA). The TOPO cloning kit was from Invitrogen, Carlsbad, Calif., USA. QIAprep spin columns were from Qiagen Inc., Valencia, Calif., USA. Streptavidin-conjugated alkaline phosphatase, streptavidin-conjugated horseradish peroxidase (HRP), goat anti-rabbit IgG-conjugated HRP, goat anti-rabbit IgG-conjugated alkaline phosphatase, immunopure streptavidin, carbonate buffer and Superblock Buffer were from Pierce Biotechnology, Rockford, Ill., USA. Fluor-coated TLC plates for UV shadowing were purchased from Ambion, Austin, Tex., USA.

Bacterial Strains and Sample Preparation

*F. tularensis* subspecies *holarctica* live culture from CDC was grown in brain heart infusion media with 0.1% cystine. Tubes were incubated at 37° C. with 5% CO2. After 48 h growth samples were boiled for 1 h to heat kill viable organisms. Killed bacteria were centrifuged at 6000 rpm in a sorvall ss34 rotor for 30 min. The bacterial pellet was washed with phosphate-buffered saline (PBS) once and finally resuspended in PBS and stored at −80° C. until further use. Formalin-killed *F. tularensis* subspecies *japonica* bacterial suspension was washed with PBS twice and resuspended in PBS for further use. To prepare total bacterial protein lysate, the suspension was frozen in liquid nitrogen and thawed on ice. The samples were freeze-thawed for two more times and vortexed for 1 min and used. An aliquot of the lysate was used to determine total protein concentration. All the lysates were stored at −80° C. until further use. *F. tularensis* subspecies *tularensis* (SCHU 4) was supplied in PBS in the concentration of $10^8$ bacteria/ml. *B. henselae* was grown in tryptic soy broth (TSB) media at 37° C. in a 5% CO2 incubator without shaking. *F. tularensis* (type B) isolated from cat serum was grown in the same media as subspecies *holarctica* at 37° C.

EXAMPLE 1

Antitularemia Aptamer Cocktail

We isolated and used aptamers of the following sequences:

```
SEQ ID NO: 1. FTJ-01:
5' TAA CCA CAA CCT TAC CAA CGA ATA

GAT TCA CCT CTC CCC ACA 3'

SEQ ID NO: 2. FTJ-02:
5' AAA CAC ACA TAC CAA TAC CCA TCA

CAT TAC TGA ACT CCA ACC 3'

SEQ ID NQ: 3. FTJ-03:
5' AAA TTC ACT CAC TAT AAA ACC CTC

GAC ATC TAA CCC CCC AAC 3'

SEQ ID NO: 4. FTJ-04:
5' GCC ATA ATA CAC CCC GCT CAC CTC

GTA TAT TCC TAA CTC CCC 3'

SEQ ID NO: 5. FTJ-05:
5' ACC CTA ACT AAC TTC ATT ATT TCC

CAC TGG AGG TAC GAA GAT 3'

SEQ ID NO: 6. FTJ-07:
5' TAT AAC ACT CCC CAT ACA TAT

ACT CGA TAT CCA CCT ACA GCA 3'

SEQ ID NO: 7. FTJ-08:
5' ATT ACA TCC TCG ACA TAA ACC ACA

CGC TCA ACA CAA CCC TGA 3'

SEQ ID NO: 8. FTJ-09:
5' ACA CTC TAA CTC AAA TCG ACT TCC

TCG AAA 3'

SEQ ID NO: 9. FTJ-11:
5' CAA TTT TCC GTC CTT ATT TAC TTT

TAA TTC TCA GCA CCC GAA 3'

SEQ ID NO: 10. FTJ-12:
5' TCA CCA ACT ACA ATT ACT CAT CTC

CCT ATA AGT TCC CCA TCA 3'

SEQ ID NO: 11. FTJ-13:
5' AAC AAT ACT TAA TAC TGC TTC CCA

CAC TCT CAT CGC CCC GTA 3'

SEQ ID NO: 12. FTJ-14:
5' CAC CAT ATC TAC TCA CAT ATC CTA

TAA ACA ACA GCA CTA CCA 3'

SEQ ID NO: 13. FTJ-15:
5' ACA CTT CAT AAC ATT TAG ACC CTC

TTT CAC AAT CCA CGC CCA 3'

SEQ ID NO: 14. FTJ-16:
5' TAC CAT TTT ATT ACC ATA TCA TAC

GGC ACA ACA TAA CCC TGA 3'

SEQ ID NO: 15. FTJ-17:
5' ACA TTG ACC GAC CAA TAC ATT ACC

TAT ACC TAT TCC CGA GCA 3'

SEQ ID NO: 16. FTJ-20:
5' ATT ACA TCC TCG ACA TAA ACC ACA

CGC TCA ACA CAA CCC TGA 3'

SEQ ID NO: 17. FTJ-21:
5' ACT TTT TAC ATC ACT TCT CCT CTG

CCA TTC ACC AAG TGA TCC 3'

SEQ ID NO: 18. FTJ-22:
5' ACT ACC TAA CAC CTA CCT TCC CTC

CCA TCG TCC GCT GCA CAG 3'

SEQ ID NO: 19. FTJ-23:
5' AAC TGA CCT TAA CAC ATA CCA TTC

TCG ATA CGG ACC TGC ACC 3'

SEQ ID NO: 20. FTJ-25:
5' ACA CAC TAA CCA CAA CCT TAA TAA

TCC CAC TGT TTC CCC CAA 3'

SEQ ID NO: 21. FTJ-27:
5' ATC CTC GAC AAA CAC TCC AAT CCG

CCT TCA TTT AAT CTC CA 3'

SEQ ID NO: 22. TJ-28:
5' ACA ACA CAC CTA AAT CCA TAA TCC

CCA TCA TCT ACT AAG CCT 3'

SEQ ID NO: 23. FTJ-29:
5' ATC TTA CCA CAT TAA TTC AAC CCG
```

-continued
CAT CAA ACC AAC TCC TCA 3'

SEQ ID NO: 24. FTJ-30:
5' AAA TTC ACT CAC TAT AAA ACC CTC

GAC ATC TAA CCC CCC AAC 3'

SEQ ID NO: 25. FTJ-32:
5' ACA AAT ACT TTA ACC TAA ACA TCC

ACC GCC GAT TCC CCA ACA 3'

Materials and Methods: Random Library and Primers

A 102-base ssDNA template containing 42 bases of random sequence flanked by defined primer-binding sites was synthesized by Sigma/Genosys:

```
                                           (SEQ ID NO: 26)
5'-ACC CCT GCA GGA TCC TTT GCT GGT ACC NNNN
(N = 42)

(SEQ ID NO: 27)
AGT ATC GCT AAT CAG TCT AGA GGG CCC CAG AAT-3'
```

The pool was then amplified via polymerase chain reaction (PCR) using 5' biotin labeled and 3' primers and it was further purified by denaturing polyacrylamide gel electrophoresis. After UV shadowing, ssDNA bands were cut and eluted from the gel. Following ethanol precipitation, the ssDNA pool was recovered by centrifugation at 4° C. and resuspended in Tris-EDTA (TE) buffer and finally used in the in vitro selection process.

In Vitro Selection Procedure

Iterative rounds of selection and amplification of ssDNA aptamers were performed as described previously by Vivekananda and Kiel in Methods and Components for Aptamers Against Anthrax, U.S. Pat. No. 6,569,630 B1 issued on May 27, 2003, hereby incorporated by reference. In brief, to exclude filter binding ssDNA sequences from the pool, the DNA was passed through a 0.45 μm HAWP filter (Millipore, Bedford, Mass., USA) and washed with an equal volume of binding buffer containing 20 mM Tris-HCL, pH 7.5, 45 mM sodium chloride, 3 mM magnesium chloride, 1 mM ethylenediaminetetra acetic acid (EDTA), 1 mM diothiothreitol (DTT). In the present study, ssDNA pools of 500 pmol for initial rounds and 200 pmol for later rounds were used in the selection process. ssDNA pools were heat-denatured at 94° C. for 3 min, and then cooled immediately to 4° C. in binding buffer. Selection was performed by incubating ssDNA pools with 100 μg of total bacterial protein (killed bacteria) at room temperature for 1 h in binding buffer by gentle rotation. After 1 h the aptamer-bacterial antigen complex was vacuum-filtered over a HAWP filter at 5 p.s.i. and washed three times with binding buffer. ssDNA that had been retained on the filter was eluted with 7M urea, 100 mM MES (4-morpholineethansulfonic acid (pH 5.5)) and 3 mM EDTA by boiling. Eluted ssDNA was then precipitated with an equal volume of isopropyl alcohol. Selected ssDNAs were amplified by PCR and used for the next round of selection. After round 10, the pool was amplified by PCR and the product was cloned using a Topo TA cloning kit (Invitrogen, Carlsbad, Calif., USA). The cloned sequences were transformed into Escherichia coli. In all, 35 colonies were picked randomly and the plasmid DNA was purified by mini-prep Qiagen kit and sequenced. In all, 25 unique sequences were obtained and used for further analyses.

Results: Selection of Anti-Tularemia Aptamers from Combinatorial Library.

DNA aptamers specific for F. tularensis subspecies japonica were selected from a library of ssDNA with a 42-nucleotide random region flanked by 27-nt 5' and 30-nt 3' fixed regions for PCR amplification. The initial library theoretically contained $10^{14}$-$10^{16}$ different sequences. Amplification was performed with biotin labeled primer F (5') and nonbiotinlabeled primer R (3') during SELEX selection. For our application, we choose to use DNA rather than RNA sequences because, with and without terminal modifications, they have been shown to be effective in biological fluids and are generally nuclease resistant. We used F. tularensis subspecies japonica antigen because this is the only type available for tularemia detection by the commercially available test kit. Prior to the selection process, the ssDNA pool was amplified to enrich the sequence pools. Upon mixing with the tularemia antigen, oligomers from the library may bind to the target DNA. During this process a bound candidate or candidates of the pool may be specific for the target and can be amplified with primers F and R. The number of PCR cycles was also optimized to avoid over-amplification. The stringency of the selection was controlled by adjusting the antigen concentrations, buffer conditions and the washes. During the process of binding and amplification, there is a possibility that some of the sequences can bind nonspecifically to the membranes. To circumvent this problem, negative selection was performed after rounds 3, 6 and 9 by passing DNA pool through nitrocellulose filters. Biotinylated DNA sequences exhibiting affinity to the target were captured by agarose-conjugated streptavidin beads. The affinity selection was stopped after 10th round, and the candidates from the pool were cloned. In all 35, randomly picked clones were isolated and the segment of DNA exhibiting unique sequences was sequenced. Out of 35 sequences, 25 were unique and the remaining 10 were duplications.

EXAMPLE 2

Aptamer-Linked Immobilized Sorbent Assay

This example involved an ELISA-like format diagnostic system for the diagnosis of tularemia in clinical samples or the presence of Francisella tularensis in environmental samples using aptamers instead of antibodies for capturing and reporting the presence of the tularemia bacteria. Twenty-five unique DNA sequence aptamers were used for this purpose on a microtiter plate platform. Possible uses include diagnosis of tularemia infection in military personnel or exposure (from environmental samples) to this biological agent, as the result of a biowarfare, bioterrorism, or natural exposure event. Another possible use is diagnosis of natural infections of tularemia in a hospital setting. One purpose of this example was to construct an aptamer-based, ELISA-like assay (ALISA) to replace the current immunoagglutination and antibody-based ELISA assays for the diagnosis of tularemia. A highly durable, reliable field test that minimizes secondary infection is preferred. The ALISA test, giving results equal or better than antibody-based tests, meets these criteria.

Materials and Methods: Aptamer-Linked Immobilized Sorbent Assay

Sandwich ALISA assays were performed in 96-well microtiter plates (Corning, supplied by Fischer Scientific, Houston, Tex., USA). The selected aptamer cocktail was coated with a concentration of 500 pmol/well and the non-specific sites were blocked with Superblock (Pierce Biotechnology). In brief, a cocktail of aptamer stock was made by reconstituting the lyophilized aptamers in sterile distilled water. The cocktail was then diluted to desired concentration in carbonate buffer pH 9.4 (Pierce Biotechnology). In all, 100 µl of the solution containing aptamers was added to each well in a 96-well clear plate and incubated for 2 h at room temperature. After the designated time, 100 µl of Superblock blocking buffer was then added on top of the aptamer solution. Plates were allowed to stand for an additional 30 min at room temperature. The contents were discarded from the plates and washed once with 200 µl of Superblock blocking buffer and dried. Prior to the binding assay, the wells were further blocked with 1% BSA in PBS for 30 min at room temperature. Various quantities ranging from 25 ng to 2 µg of total bacterial antigen from *F. tularensisis* subspecies *japonica*, were incubated for 1 h at room temperature by gentle shaking in 100 µl of binding buffer containing 20 mM Tris-HCL, pH 7.5, 45 mM sodium chloride, 3 mM magnesium chloride, 1 mM EDTA, 1 mM diothiothreitol (DTT). After the designated time, unbound target was removed and the plates were washed twice with 0.1% Tween-20 in PBS (phosphate-buffered saline/Tween (PBS-T)). After the final wash, biotin-labeled aptamer cocktail was then added to the individual wells at a concentration of 500 pmol/well. The plates were further incubated at room temperature for another hour. Unbound biotin aptamers were removed and the plates washed twice with PBS-T. Finally 100 µl of a 1:1000 dilution of a solution of streptavidin conjugated to HRP were added to the individual wells. Following 30-min incubation at room temperature on a shaking platform, wells were washed twice with PBS-T and developed using ABTS as substrate (Sigma) according to the manufacture's instructions, and absorbance was read at 405 nm using Synergyt HT Multi-Detection Microplate Reader from BIO-TEK. Antigens from *F. tularensis* subspecies *holarctica* and *tularensis* (SCHU 4) were used to assess the specificity of the aptamers. *B. henselae*, chicken albumin and chicken lysozyme were used as negative controls.

Enzyme-Linked Immunosorbent Assay

To compare aptamer cocktail vs anti-tularemia antibodies, we developed a sandwich Enzyme linked Immunosorbent Assay (ELISA) assay using commercially available *F. tularensis* rabbit antiserum (Becton-Dickinison and Company). Antiserum was diluted to 1:1000 with carbonate-bicarbonate buffer (pH 9.0). Ninety-six-well microtiter plates (Corning) were coated with 100 µl of diluted antiserum for 1 h at 37° C. The wells were washed further with PBS-T (0.01%; pH 7.2) and blocked with Superblock for 30 min and dried at room temperature. Following further blocking with 1% BSA in PBS, *F. tularensis* subspecies *japonica* antigen was added to the wells in quantities ranging from 25 to 500 ng, and 1 to 2 mg in PBS. After an incubation of 1 h at room temperature, wells were washed with PBS-T three times. After removal of unbound antigen, the wells were probed with anti-tularemia rabbit IgG at a dilution of 1:1000 for 1 h. After plates had been washed thrice with PBS-T, 100 µl of horseradish peroxidase (Pierce Biotechnology, Rockford, Ill., USA) conjugated goat anti-rabbit IgG at a dilution of 1:5000 was added to the wells and allowed to bind for 30 min. After three washes with PBS-T, the enzymatic reaction was started with 100 µl of ABTS (Sigma) according to the manufacturer's recommendation. $OD_{405}$ values were determined using a microplate reader from BIO-TEK. As for the ALISA, antigens from subspecies *holarctica* and *tularensis* (SCHU 4) were used in the ELISA. *Bartonella henselae*, chicken albumin and chicken lysozyme were used as negative controls.

Results: Binding Affinity of DNA Aptamers to *F. tularensis* subspecies *japonica* by Aptamer-Linked Immobilized Sorbent Assay (ALISA)

To determine the affinity of the selected polyclonal DNA aptamer cocktail for *F. tularensis* japonica antigen we developed an Aptamer-Linked Immobilized Sorbent Assay. This assay provided a rapid assessment of the relative binding capabilities of this aptamer cocktail. Additionally, this enzymatic assay (ALISA) was used to provide information of specificity of these aptamers to tularemia antigen from other subspecies. In this format, a nonbiotinylated aptamer cocktail was immobilized as a capture aptamer as described in the methods. Tularemia antigen from subspecies *japonica* was added to the wells with quantities ranging from 25 ng to 2 µg. Target molecule sensitivity was assessed for these aptamers by determining their binding affinity. Binding reaction was carried out as described in the earlier section. Employing a colorimetric detection system (ABTS) for horseradish peroxidase activity conjugated to streptavidin, we observed a significant signal over background, and data for four replicate samples ranged from 0.0451 (background) to 1.667 absorbance units.

Figure 1:
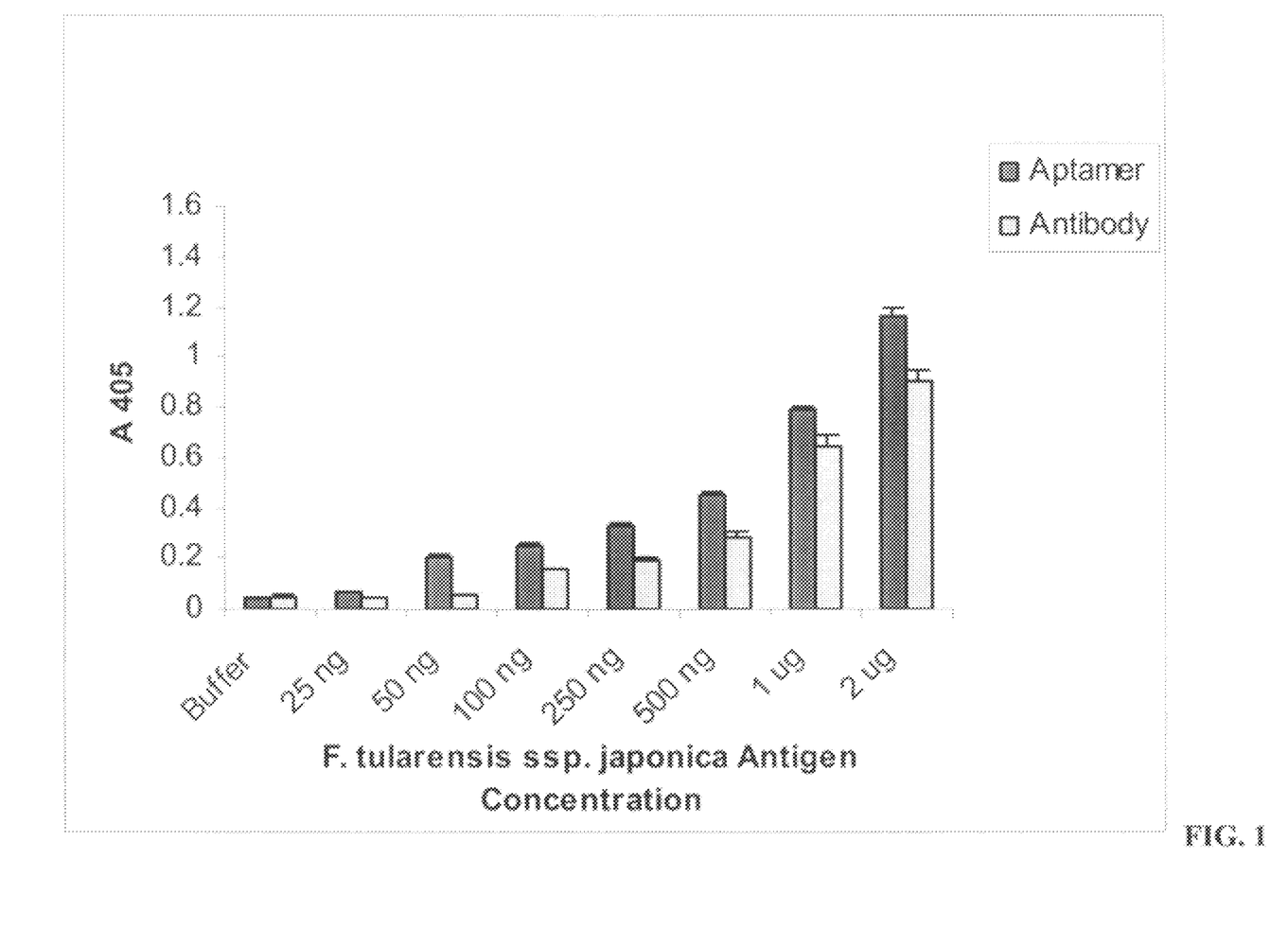
FIG. 1 is a graph illustrating an example of the sensitivity of anti-tularemia aptamer cocktail for F. tularensis subspecies japonica antigen and anti-tularemia antiserum as assessed by ALISA and ELISA.

FIG. 1 is a graph illustrating an example of the sensitivity of anti-tularemia aptamer cocktail for *F. tularensis* subspecies *japonica* antigen and anti-tularemia antiserum as assessed by ALISA and ELISA. The assays were performed as described in 'Materials and methods'. The data are presented as OD at 405 nm vs antigen quantity. Averages of four replication measurements are shown in the figure. As seen in FIG. 1, it is further confirmed that the antigen affinity to the aptamer cocktail is directly proportional to the quantity of antigen. It is evident from the data that aptamers exhibit impressive binding affinities for subspecies *japonica* achieving an unusually strong association even at 25 ng of total antigen. While it is clear that the detection limit depends primarily on the binding affinity of aptamers for the target, the formation of an affinity-based complex is also a step in producing signal. In order to achieve an absolute assessment of target molecule sensitivity in terms of number of bacteria, an ALISA was performed with subspecies *holarctica*. Here, various concentrations of bacteria were prepared by serial dilution with PBS and used in the binding assay.

Figure 2:
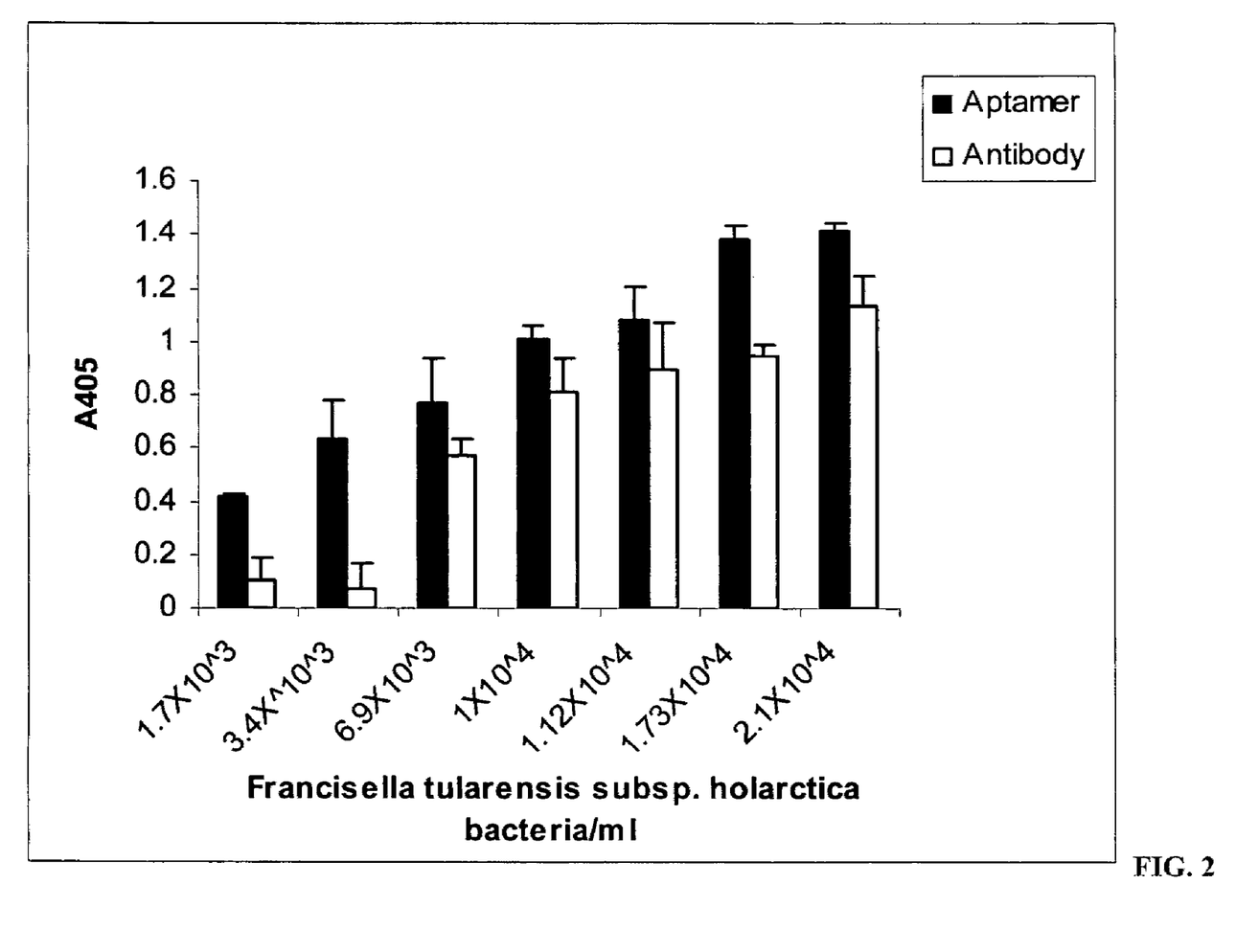
FIG. 2 is a graph illustrating an example of tularemia bacterial antigen binding to anti-tularemia aptamer cocktail and anti-tularemia polyclonal antibodies as assessed by ALISA and ELISA using HRP activity.

FIG. 2 is a graph illustrating an example of tularemia bacterial antigen binding to anti-tularemia aptamer cocktail and anti-tularemia polyclonal antibodies as assessed by ALISA and ELISA using HRP activity. The assays were performed as described in 'Materials and methods'. The bacterial antigen used in the binding assay was prepared from *F. tularensis* subspecies *holarctica* (live vaccine strain). The data are plotted as OD at 405 nm vs number of bacteria/ml. Averages of triplicate measurements are shown in the figure. The data presented in FIG. 2 demonstrate that the sensitivity and detection of the target is attained as low as $1.7 \times 10^3$/ml of bacteria. It is interesting and perhaps paradoxical to note that these two different subspecies exhibited a similar binding affinity thereby indicating the detection capability of aptamers in this platform across the subspecies. In order to verify the specificity of the aptamer cocktail to other *F. tularensis* subspecies, we tested the binding affinity of these aptamers against antigens from two other subspecies *holarctica*, *tularensis* (SCHU 4), and another isolate (#38) type B (Houston, Tex., USA) which was positive for agglutination and negative for glycerol fermentation. Also the isolate #38 was further confirmed as type B by PCR amplification of ISFtu2 element using the CDC's primer sequences (data not shown). The specificity of the aptamer cocktail was further evaluated by ALISA using antigens from three other subspecies listed earlier.

Figure 3:
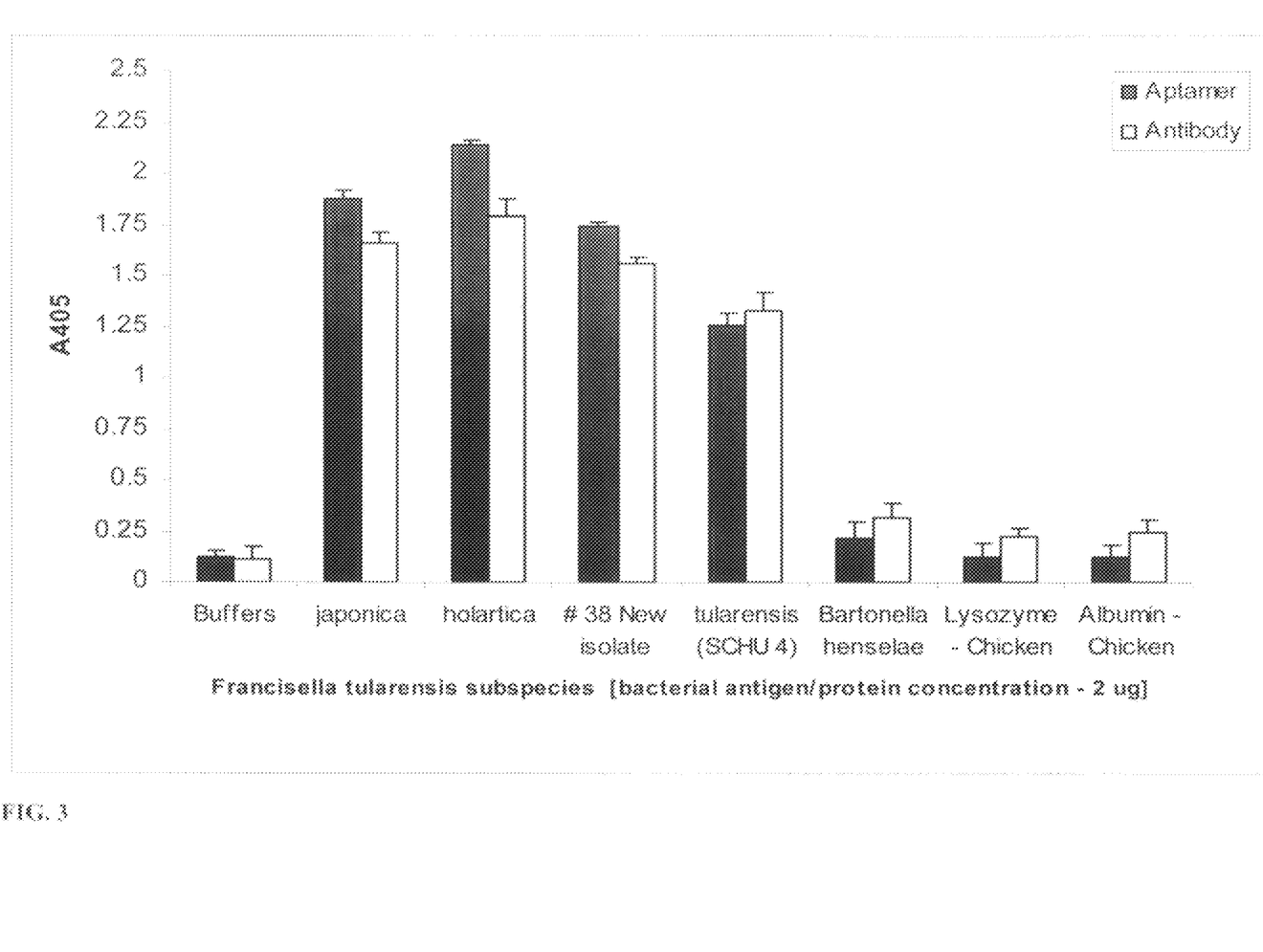
FIG. 3 is a graph illustrating an example of ALISA and ELISA to analyze the specificity of anti-tularemia aptamer cocktail.

FIG. 3 is a graph illustrating an example of ALISA and ELISA to analyze the specificity of anti-tularemia aptamer cocktail. The assays were performed as described in 'Materials and methods'. Antigen from both type A and B of *F. tularensis* are used in the analysis. Subspecies include *holarctica*, #38 (type B) a new isolate from Houston, *tularensis* (SCHU 4) and an unrelated Gram-negative rod shaped bacteria *B. henselae*. Additional negative controls include chicken lysozyme and chicken albumin. As can be seen in FIG. 3 the signal output is ranging from 1.256 for subspecies *tularensis* (SCHU 4) to 2.144 absorbance units for subspecies *holarctica*, indicating a substantial homology with common motifs for binding and cross reactivity between the subspecies. Finally, to rule out the nonspecificity of the aptamers, antigen from unrelated bacteria and other pure proteins were used in the assay. Sandwich ALISA and ELISA assays were carried out with total antigen from *B. henselae* a rod-shaped Gram-negative bacteria showed a very low affinity. However *B. henselae* exhibited some nonspecific binding with both aptamer and antibody. This most likely is due to some similar bacterial wall components because both of these bacteria are Gram negative. In contrast, pure proteins like chicken albumin and lysozyme showed no affinity with an optical density close to background.

Anti-Tularemia Polyclonal Antibody Specificity for Tularemia Antigen by ELISA

To compare aptamer specificity to that of antibodies, we performed a sandwich ELISA using commercial antiserum. The ELISA plates were coated with antitularemia rabbit antiserum as described in methods. Identical quantities of subspecies *japonica* total antigen are used in the binding assay. The data presented in FIG. 1 indicates that antibody is not as sensitive as aptamer cocktail. Furthermore, the detection limit for aptamer cocktail is 25 ng whereas the detection limit for antibody was 100 ng of antigen. Similar to aptamers, antibody exhibited concentration-dependent signal output in the ELISA. An attempt was made to assess the binding affinity of antibody to other related and unrelated antigens. To compare the detection capability of antibody in terms of bacterial cell number, similar to ALISA, whole *F. tularensis* holarctica antigen was used in the ELISA. In this assay, the diagnostic performance of the ELISA is inferior to the ALISA as depicted in FIG. 2. While the aptamer cocktail can detect $1.7 \times 10^3$ bacteria/ml, (Absorbance units=0.413), the threshold for antibody detection is $6.9 \times 10^3$ bacteria/ml (Absorbance units=0.568). Further binding assays with identical quantities of total antigen from all the three subspecies *holarctica, japonica* and *tularensis* (SCHU 4) along with unrelated *B. henselae* and pure proteins from chicken were performed to compare the ELISA to the ALISA. As shown in FIG. 3, the antibody detected the antigen from all the three subspecies of *F. tularensis* by generating positive signal in the enzymatic assay. As expected, there were negative signals for pure proteins from chicken. Additionally, we observed some nonspecific binding to *B. henlselae*. This could be partly due to the fact that the serum may have had some products binding nonspecifically to the bacteria. The other notable observation under identical conditions is that the antibody exhibited a higher level of nonspecific binding affinity with albumin and lysozyme (FIG. 3) compared to aptamer cocktail, indicating significant advantages of aptamers over their antibody counterparts. Although antibody-based detection systems are available, the presented data reinforce the superior performance of the aptamer-based detection/diagnostic system.

The significant difference in response of the ALISA between the SCHU 4 (Type A) and the other Type B F.t. indicates that amongst the 25 aptamers used some will only bind to Type B but not to Type A. Therefore, the ALISA, unlike the immunoassays, has the potential to distinguish the two types without culture. Furthermore, the DNA aptamers are more stable compared to antibody (not requiring refrigeration or special handling) and can be produced wholly synthetically or in a bacterial host. Therefore, unlike antibody, eukaryotic cells (hybridomas) or animals are unnecessary to produce aptamers, greatly reducing the time and expense of selection and production.

EXAMPLE 3

Dot Blot

Materials and Methods: Dot Blot Analysis with Aptamers and Antibodies.

Fifty µg of bacterial lysate from *F. tularensis* subspecies holartica, #38 isolate and *tularensis* (SCHU 4) were spotted onto nitrocellulose membrane discs and allowed to air dry. These samples were fixed under vacuum at 80° C. for 1 h and blocked with 5% BSA in PBS. One batch was incubated with biotin-labeled aptamer cocktail at 500 pmol/disc in binding buffer (20 mM Tris-HCl, pH 7.5, 45 mM sodium chloride, 3 mM magnesium chloride, 1 mM EDTA, 1 mM DTT) for 1 h at room temperature with gentle rocking. The other batch was probed with anti-tularemia rabbit IgG (Becton-Dickinson and Company) in PBS at a dilution of 1:1000 for 1 h. After the designated time, both batches of membrane discs were washed with PBST three times and probed with streptavidin-conjugated alkaline phosphatase (Pierce Biotechnology, Rockford, Ill., USA), and goat anti-rabbit IgG-conjugated alkaline phosphatase (Pierce Biotechnology, Rockford, Ill., USA), respectively, for 30 min. Excess enzyme was removed by three subsequent washes with PBS-T. Finally, the membrane discs were developed with 5-bromo-4-chloro-3-indolylphosphate/nitro blue tetrazolium (BCIP/NTB)-BLUE (Sigma). *Bartonella henselae*, chicken albumin and chicken lysozyme were used as negative controls.

Results: Comparisons of the Specificity of the Anti-Tularemia Aptamer Cocktail to Anti-Tularemia Polyclonal Antibody Using Dot Blot Analysis The results of the ALISA and ELISA suggested that the anti-tularemia aptamer cocktail exhibited specificity for tularemia antigen irrespective of their source. In order to verify the specificity and to further investigate the potential uses of the aptamers, we performed a dot blot analysis (FIG. 4).

Figure 4:
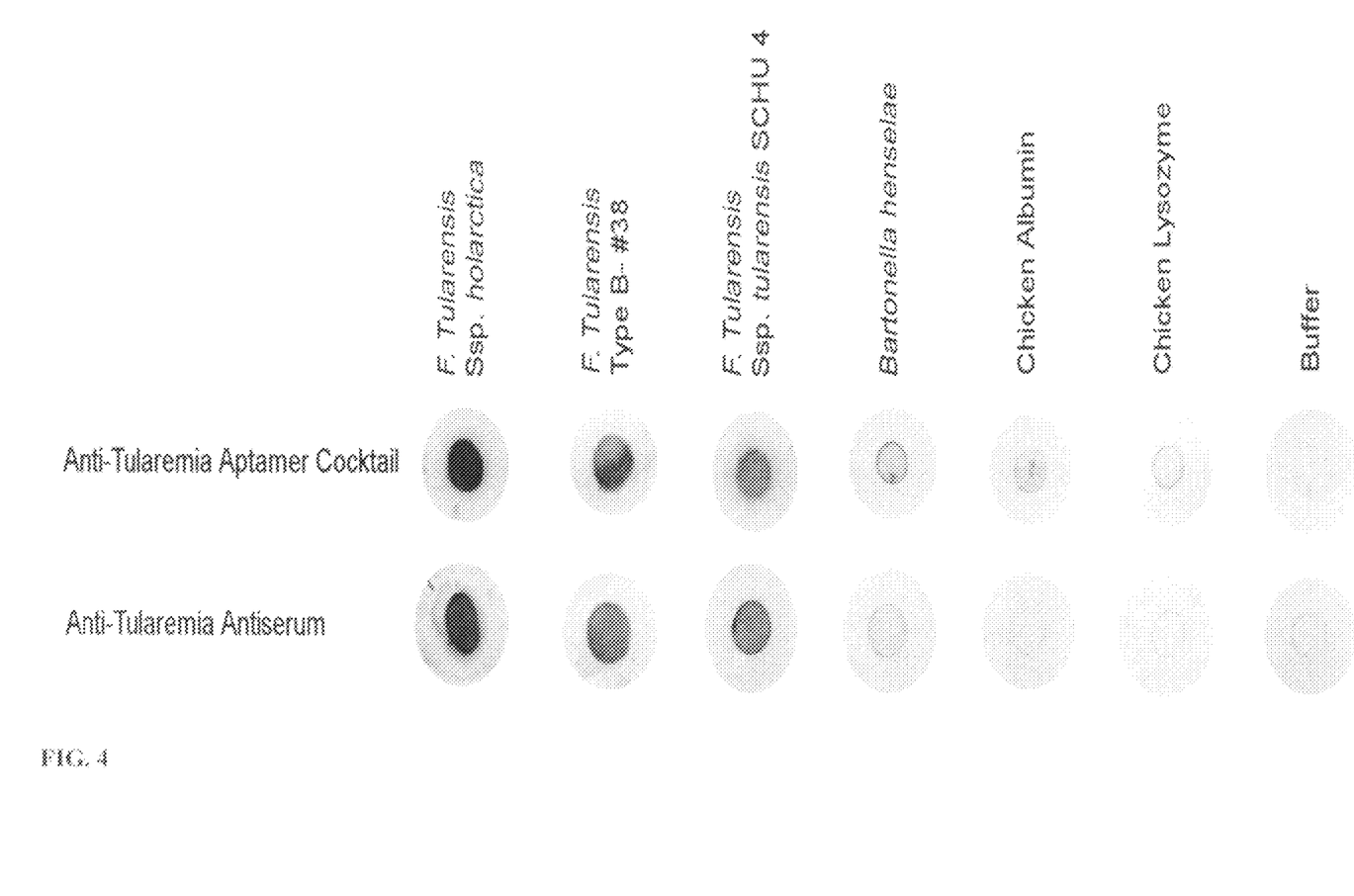
FIG. 4 is a photograph illustrating an example of the specificity of anti-tularemia aptamer cocktail and anti-tularemia antiserum assessed by dot blot analysis.

FIG. 4 is a photograph illustrating an example of the specificity of anti-tularemia aptamer cocktail and anti-tularemia antiserum assessed by dot blot analysis. Fifty micrograms of total protein from *F. tularensis* subspecies *holarctica, F. tularensis* type B an isolate (#38) from Cat (from Houston, Tex.), *F. tularensis* subspecies *tularensis* (SCHU 4), *B. henselae*, chicken albumin and chicken lysozyme were spotted onto nitrocellulose membrane discs and probed with either aptamer cocktail or anti-tularemia rabbit antiserum and analyzed by alkaline phosphatase activity by using 5-bromo-4-chloro-3-indolylphosphate/Nitro Blue Tetrazolium (BCIP/NTB)-Blue as described in 'Materials and methods'. In all, 50 µg of total protein from the bacterial lysate from subspecies *holarctica*, #38, tularensis along with *B. henselae*, chicken lysozyme and chicken albumin were spotted onto nitrocellulose discs and air dried at room temperature. To test the exquisite binding specificity of aptamers compared to their counterpart antibodies, we also performed parallel immuno 
dot blot assay with anti-tularemia antiserum. The immobilized proteins were probed with biotin labeled aptamer cocktail and detected with streptavidin conjugated alkaline phosphatase. Parallel blots were treated with tularemia antiserum and developed with alkaline phosphatase conjugated goat anti-rabbit antibody. As shown in FIG. 4, the signal/color produced by the aptamer cocktail and antibody showed strong affinity to tularemia bacterial lysate but did not show any affinity to negative controls, thereby indicating their specificity towards the antigens of different subspecies of *F. tularensis*. Interestingly, in this 
27 Isherwood K E, Titball R W, Davies D H, et al. Vaccination strategies for *Francisella tularensis*. Adv Drug Delivery Rev 2005; 57:1403-1414.

28 Vivekananda J, Kiel J L. Methods and components for aptamers against anthrax. U.S. Pat. No. 6,569,630 B1 issued on May 27, 2003.

29 Tasset D M, Kubik M F, Steiner W. Oligonucleotide inhibitors of human thrombin that bind distinct epitopes. J Mol Biol 1997; 272:688-698.

30 Griffin L C, Toole J J, Leung L L K. Discovery and characterization of a novel nucleotide-based thrombin inhibitor. Gene 1993; 137:25-31.

31 Hicke B D, Watson S R, Koenig A, et al. DNA aptamers block L-selectin function in vivo. J Clin Invest 1996; 98:2688-2692.

31 Petersen J M, Schriefer M E, Carter L G, et al. Laboratory analysis of tularemia in wild-trapped, commercially traded prairie dogs, Texas, 2002. Emerging Infectious Diseases 2004; 10:419-425.

33 Ivnitski D, O'Neill D J, Gattuso A, et al. Nucleic acid approaches for detection and identification of biological warfare and infectious disease agents [Review]. Biotechniques 2003; 35:862-869.

Huang D B, Vu D, Cassidy L A, et al. Crystal structure of N-kB (P50)2 complexed to a high-affinity RNA aptamer. Proc Natl Acad Sci USA 2003; 100:9268-9273.

35 Jenison R D, Gill S C, Pardi A, et al. High-resolution molecular discrimination by RNA. Science 1994; 263:1425-1429.

36 Petrenko V A, Sorokulova I B. Detection of biological threats. A challenge for directed molecular evolution [Review]. J Microbial Methods 2003; 58:147-168.

37 Drolet D W, Moon-McDermott L, Romig T S. An enzyme-linked oligonucleotide assay. Nat Biotechnol 1996; 8:1021-1025.

38 Rye P D, Nustad K. Immunomagnetic DNA aptamer assay. Biotechniques 2001; 30:290-295.

39 Yang X, Li X, Prow T W, et al. Immunofluorescence assay and flow-cytometry selection of bead-bound aptamers. Nucleic Acids Res 2003; 31:e54.

40 Lee M, Walt D R. A fiber-optic microarray biosensor using aptamers as receptors. Anal Biochem 2000; 282: 142-146.

41 Liss M, Petersen B, Wolf H, et al. An aptamer-based quartz-crystal protein biosensor. Anal Chem 2002; 74: 4488-4495.

42 Grunow R, Splettstoesser W, McDonald S, et al. Detection of *Francisella tularensis* in biological specimens using capture enzyme-linked immunosorbant assay, an immunochromatographic handheld assay and PCR. Clin Diag Lab Immunol 2000; 7:86-90.

43 Porsch-Ozcurumez M, Kischiel N, Priebe H, et al. Comparison of enzyme-linked immunosorbent assay, western blotting, muicroglutination, indirect immunofluorescence assay and flow cytometry for serological diagnosis of tularemia. Clin Diag Invest Immunol 2004; 11:1008-1015.

44 Morner T, Sandstrom G. Tularemia. Manual of Diagnostic Tests and vaccines for terrestrial animals. World Organization for Animal Health (OIE) Part 2, Ch. 2.8.2. 2004.

45 Baldrich E, Acero J L, Reekmans G, et al. Displacement enzyme linked aptamer assay. Anal Chem 2005; 77:4774-4784.

We claim:

1. A method comprising: providing a combination of aptamers comprising SEQ ID NOs: 1-25; adding a prepared sample to a microtiter plate pre-coated with the combination of aptamers; adding an aptamer cocktail, the aptamer cocktail comprising a combination of biotin-labeled aptamers comprising SEQ ID NOs: 1-25; adding a reporter comprising a streptavidin-conjugated enzyme; adding substrate; and detecting whether *Francisella tularensis* or components thereof are present in the prepared sample.

2. A method comprising: providing a combination of biotin-labeled aptamers comprising SEQ ID NOs: 1-25; fixing a prepared sample to a surface; contacting the combination of biotin-labeled aptamers with the prepared sample; adding a reporter comprising a streptavidin-conjugated enzyme; adding a developer; and detecting whether *Francisella tularensis* or components thereof are present in the prepared sample.

3. A composition comprising a combination of aptamers comprising SEQ ID NOs: 1-25, wherein the combination of aptamers binds to *Francisella tularensis* or components thereof.

4. A kit comprising: packaged together, a microtiter plate pre-coated with a combination of aptamers comprising SEQ ID NOs: 1-25, wherein the combination of aptamers binds to *Francisella tularensis* or components thereof; an aptamer cocktail, wherein the aptamer cocktail comprises a combination of biotin-labeled aptamers comprising SEQ ID NOs: 1-25; wash buffer; a reporter comprising a streptavidin-conjugated enzyme; and substrate solution.

* * * * *

SEQUENCE LISTING

```
<160> NUMBER OF SEQ ID NOS: 27

<210> SEQ ID NO 1
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 1
taaccacaac cttaccaacg aatagattca cctctcccca ca                        42

<210> SEQ ID NO 2
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 2
aaacacacat accaataccc atcacattac tgaactccaa cc                        42

<210> SEQ ID NO 3
<211> LENGTH: 42
<212> TYPE: DNA
<213> ORGANISM: Artificial Sequence
<221> NAME/KEY: misc_feature
<222> LOCATION: (1)..(42)
<223> OTHER INFORMATION: Synthetic Oligonucleotide
```

<400> SEQUENCE: 3 aaaattcactc actataaaac cctcgacatc taaccccccca ac                              42

<210> SEQ ID NO 4
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 4
gccataatac accccgctca cctcgtatat tcctaactcc cc                                42

<210> SEQ ID NO 5
<211> LENGTH: 42
<212> TYPE: DNA
<213> ORGANISM: Artificial Sequence
<221> NAME/KEY: misc_feature
<222> LOCATION: (1)..(42)
<223> OTHER INFORMATION: Synthetic Oligonucleotide

<400> SEQUENCE: 5
accctaacta acttcattat ttcccactgg aggtacgaag at                                42

<210> SEQ ID NO 6
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 6
tataacactc cccatacata tactcgatat ccacctacag ca                                42

<210> SEQ ID NO 7
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 7
attacatcct cgacataaac cacacgctca acacaaccct ga                                42

<210> SEQ ID NO 8
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic Oligonucleotide

<400> SEQUENCE: 8
acactctaac tcaaatcgac ttcctcgaaa                                              30

<210> SEQ ID NO 9
<211> LENGTH: 42
<212> TYPE: DNA
<213> ORGANISM: Artificial Sequence
<220> FEATURE:

```
<221> NAME/KEY: misc_feature
<222> LOCATION: (1)..(42)
<223> OTHER INFORMATION: Synthetic Oligonucleotide

<400> SEQUENCE: 9 caatttccg tccttattta cttttaattc tcagcacccg aa                      42

<210> SEQ ID NO 10
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 10
tcaccaacta caattactca tctccctata agttccccat ca                     42

<210> SEQ ID NO 11
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 11
aacaatactt aatactgctt cccacactct catcgccccg ta                     42

<210> SEQ ID NO 12
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 12
caccatatct actcacatat cctataaaca acagcactac ca                     42

<210> SEQ ID NO 13
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 13
acacttcata acatttagac cctctttcac aatccacgcc ca                     42

<210> SEQ ID NO 14
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 14
taccatttta ttaccatatc atacggcaca acataaccct ga                     42

<210> SEQ ID NO 15
```

```
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 15
acattgaccg accaatacat tacctatacc tattcccgag ca                              42

<210> SEQ ID NO 16
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 16
attacatcct cgacataaac cacacgctca acacaaccct ga                              42

<210> SEQ ID NO 17
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 17 acttttaca tcacttctcc tctgccattc accaagtgat cc                               42

<210> SEQ ID NO 18
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 18
actacctaac acctaccttc cctcccatcg tccgctgcac ag                              42

<210> SEQ ID NO 19
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 19
aactgacctt aacacatacc attctcgata cggacctcga cc                              42

<210> SEQ ID NO 20
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 20
```
acacactaac cacaacctta ataatcccac tgtttccccc aa        42

<210> SEQ ID NO 21
<211> LENGTH: 41
<212> TYPE: DNA
<213> ORGANISM: Artificial Sequence
<220> FEATURE:
<221> NAME/KEY: misc_feature
<222> LOCATION: (1)..(41)
<223> OTHER INFORMATION: Synthetic Oligonucleotide

<400> SEQUENCE: 21
atcctcgaca aacactccaa tccgccttca tttaatctcc a        41

<210> SEQ ID NO 22
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 22
acaacacacc taaatccata atccccatca tctactaagc ct       42

<210> SEQ ID NO 23
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 23
atcttaccac attaattcaa cccgcatcaa accaactcct ca       42

<210> SEQ ID NO 24
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 24
aaattcactc actataaaac cctcgacatc taaccccca ac        42

<210> SEQ ID NO 25
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic Oligonucleotide

<400> SEQUENCE: 25
acaaatactt taacctaaac atccaccgcc gattccccaa ca       42

<210> SEQ ID NO 26
<211> LENGTH: 27
<212> TYPE: DNA
<213> ORGANISM: Artificial Sequence
<220> FEATURE:
<221> NAME/KEY: misc_feature
<222> LOCATION: (1)..27

```
<223> OTHER INFORMATION: Synthetic Oligonucleotide

<400> SEQUENCE: 26
acccctgcag gatcctttgc tggtacc                                              27

<210> SEQ ID NO 27
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: Synthetic Oligonucleotide

<400> SEQUENCE: 27
agtatcgcta atcagtctag agggcgcccag aat                                      33
```